United States Patent [19]
Thiem

[11] Patent Number: 5,711,200
[45] Date of Patent: Jan. 27, 1998

[54] CRYOSTATIC MICROTOME

[75] Inventor: Stefan Thiem, Heidelberg, Germany

[73] Assignee: Leica Instruments GmbH, Wetzlar, Germany

[21] Appl. No.: 536,284

[22] Filed: Sep. 29, 1995

[30] Foreign Application Priority Data

Sep. 30, 1994 [DE] Germany .......................... 44 34 937.8

[51] Int. Cl.⁶ .................................................. G01N 1/28
[52] U.S. Cl. .............................. 83/170; 83/915.5; 62/320
[58] Field of Search .......................... 83/170, 171, 915.5, 83/648; 62/320, 331

[56] References Cited

U.S. PATENT DOCUMENTS 5,299,481  4/1994  Lihl et al. .................................. 83/170

FOREIGN PATENT DOCUMENTS 36 03 278   9/1986   Germany .
40 28 806   9/1990   Germany .
87/02130    4/1987   WIPO .
90/14585   11/1990   WIPO .

*Primary Examiner*—Rinaldi I. Rada
*Assistant Examiner*—Boyer Ashley
*Attorney, Agent, or Firm*—Foley & Lardner

[57] ABSTRACT

A housing for a microtome which is capable of being employed in a cryostat. The microtome housing includes a waterproof microtome chamber having an elongate slot formed in the wall thereof through which an object holding device extends. The elongate slot has a seal disposed about its periphery and the slot is covered by a coverplate which is provided adjacent to the seal. The coverplate is rotatable about the axis of a pin which is provided on the interior of the chamber wall. The chamber further includes magnets which are arranged on the wall of the chamber adjacent to the elongate slot such that the magnets retain the coverplate over the elongate slot. This arrangement allows the object holding device to be easily inserted into and removed from the chamber, while at the same time maintaining substantially moisture free conditions within the chamber.

7 Claims, 3 Drawing Sheets

CRYOSTATIC MICROTOME

BACKGROUND OF THE INVENTION

1. Field of the Invention

The invention relates to a cover device or housing for a cryostatic microtome assembly.

2. Description of Related Art

Cryostatic microtomes are designed for cooling objects to be cut to a specific predetermined temperature. The temperatures are, as a rule, between −10° C. and 50° C. In order to guarantee constancy, that is, uniformity of temperature, the microtomes are usually arranged in housings and/or encased in a complicated manner. A disadvantage associated with these types of housings however, is, inter alia, that the microtomes are cooled together with the object to be cut. After a cutting operation and thawing is permitted to occur, atmospheric moisture collects on the microtome which may damage or harm the mechanism of the microtome. For this reason and others, it was decided to arrange the microtomes in separate chambers within the cryostat. In this case, the movable object holder of the microtome has to be inserted through the chamber wall into the cooling region of the cryostat. Thus, a difficulty arises in designing a passage in such a way that, in addition to allowing for unimpeded functioning of the object holder, sealing-off against penetrating moisture is also guaranteed. That is, it is difficult to design a passage in the chamber which is adapted to allow the object holder to be introduced into the chamber while at the same time ensuring that the entire chamber is moisture proof.

A housing for a microtome is known from DE 36 03.278 C1. The microtome housing has an elongate slot, through which a movable object-holding device extends. The elongate slot is covered by a pivotably mounted coverplate. The coverplate possesses, furthermore, a bearing orifice which is designed as a long hole. A pin arranged on the microtome housing engages into the long hole. This housing, although useful in connection with non-cryostatic microtomes, is not easily adapted for use in a cryostat.

SUMMARY OF THE INVENTION

One object of the present invention is, therefore, to provide a housing for a microtome which is capable of being used in a cryostat.

This object is achieved, according to the invention, by providing a housing for a microtome which is capable of being employed in a cryostat comprising a waterproof microtome chamber having an elongate slot formed in the wall thereof, through which an object holding device extends. The elongate slot has a seal disposed about its periphery and the slot is covered by a coverplate which is provided adjacent to the seal. The coverplate is rotatable about the axis of a pin which is provided on the interior of the chamber wall. The chamber further includes magnets which are arranged on the wall of the chamber adjacent to the elongate slot such that the magnets retain the coverplate over the elongate slot. This arrangement allows the object holding device to be easily inserted into and removed from the chamber, while at the same time maintaining substantially moisture free conditions within the chamber.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
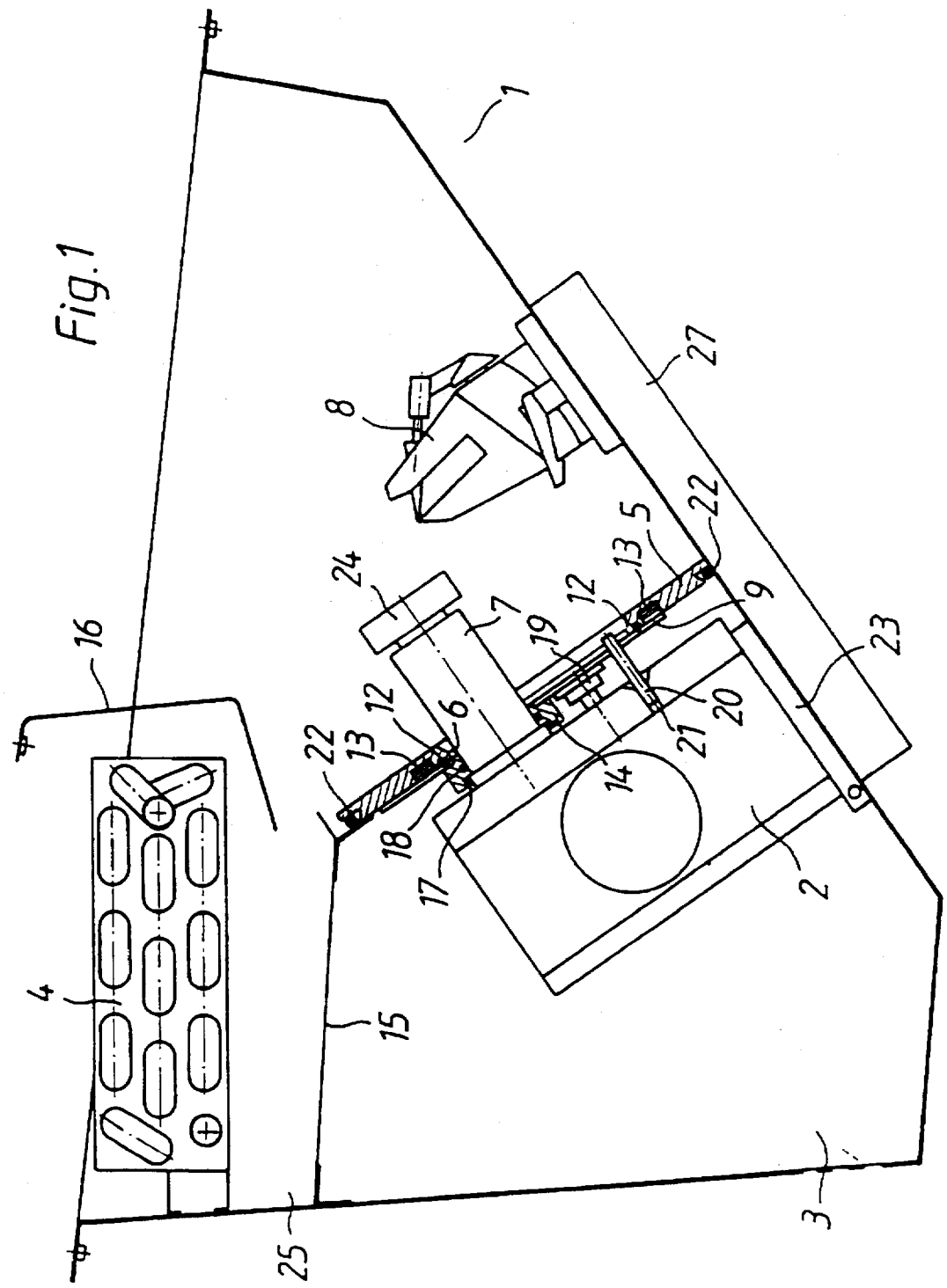
FIG. 1 shows a sectional view of a cryostat which includes a separate microtome chamber according to the present invention.

FIG. 1 shows a cryostatic microtome assembly 1 with a baseplate 27, a cryostat 25, a refrigerating device 4, an evaporator screen 16 and a knife holder 8. Provided in the cryostat 25 is a separate chamber 3 for holding a microtome 2, which is separated from the remaining cryostat 25 by means of a stationary side wall 15 and a releasably fastened chamber wall 5. The cryostat 25 is cooled by the refrigerating device 4 from −10° C. to −50° C. The separate chamber 3 can reach similar temperatures as the cryostat 25 since the separate chamber 3 preferably includes only a metal wrapping without heat insulation. The microtome 2 is fastened releasably to a holding plate 23 and has an orifice 21 for receiving a locating pin 20 fastened to the chamber wall 5. The microtome 2 has a linearly oscillating, that is, an axially movable object-holding device 7 with an object holder 24. The object-holding device 7 extends through a sleeve 14 which is fastened to a pivotably mounted coverplate 9. The coverplate 9 is arranged above an elongate slot 6 provided in the chamber wall 5. The coverplate 9 and sleeve 14 are tightly mounted together and form a unit.

The coverplate 9, which is preferably formed of a magnetic material or metal, covers the free orifice of the elongate slot 6 and slides on a plastic seal 12 surrounding the orifice. For the retention of the coverplate 9, there are arranged on the chamber wall 5 two magnets 13 which have a smaller thickness than the thickness of the peripheral seal 12, so that a narrow gap is formed between the magnets 13 and the coverplate 9. This ensures that, in addition to a secure retention via the magnets 13, an unimpeded movement of the coverplate 9 over the seal 12 is also possible.

To render the microtome chamber 3 waterproof, the chamber wall 5 has a peripheral seal 22 which is provided between the stationary side wall 15 and the removable chamber wall 5. The chamber wall 5 is fastened via a holding magnet 19 arranged on the microtome 2.

In addition, a waterproof seal is also provided between the sleeve 14 and the object-holding device 7 via a peripheral seal 18.

For driving the pivotably mounted coverplate 9, a rotating guide band 17 is provided between the sleeve 14 and the object-holding device 7 moved in a linear or axial direction. The rotating guide band 17 transfers the linear movement of the object holding device 7 and softens the sound and the friction. The cover plate 9 allows a turning movement around the pin 11 and has a gliding movement over the orifice 10 overlapping it.

A baseplate 27 is provided as a carrier for the microtome 2 and for the knife holder 8 outside the cryostat 25. This arrangement allows the cryostatic microtome assembly 1 to be easily cleaned after the removal of the microtome 2 and the knife holder 8.

Figure 2:
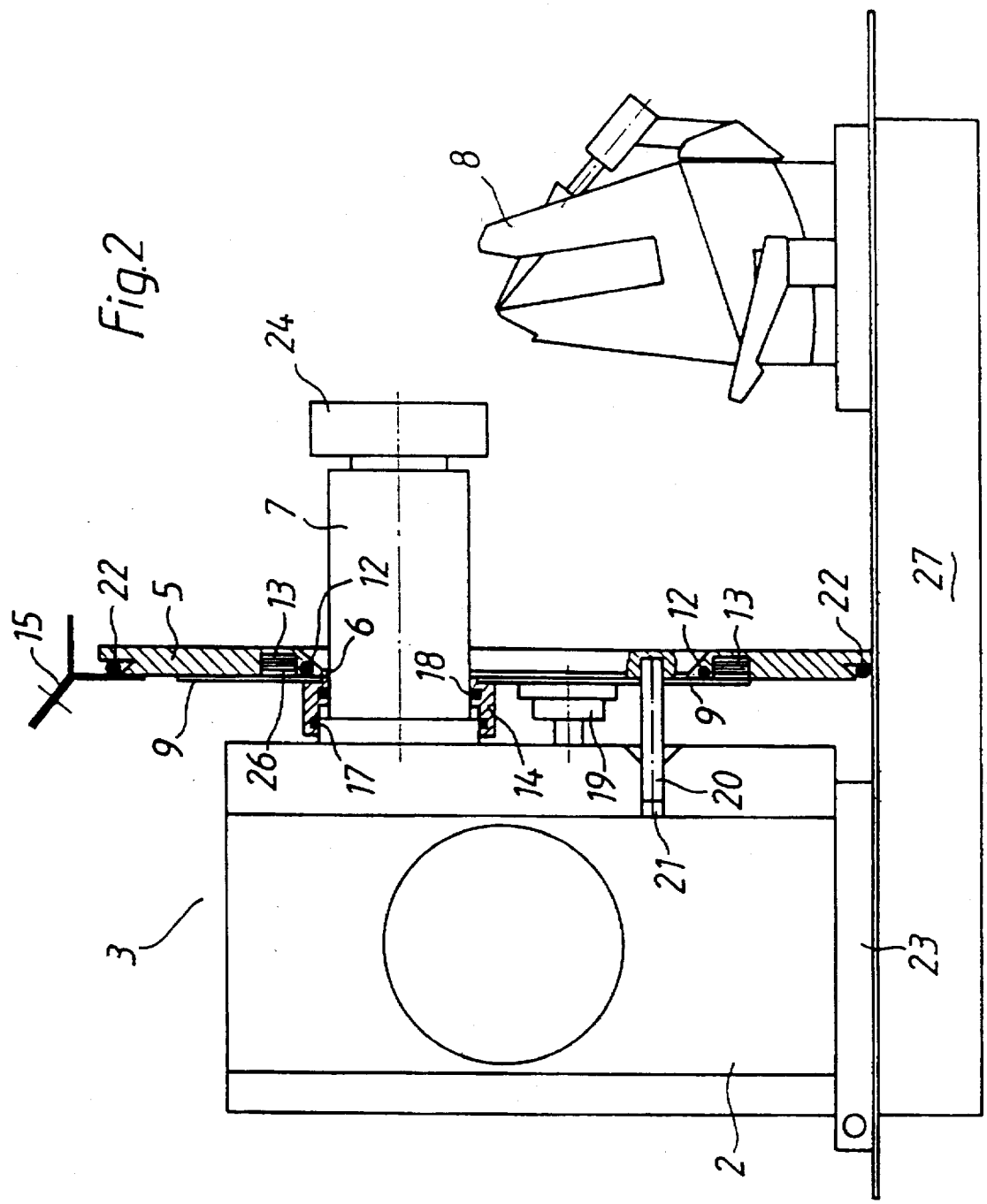
FIG. 2 shows a sectional view of a chamber wall.

FIG. 2 shows a detail of FIG. 1 with the coverplate 9, the elongate slot 6 and the plastic seal 12. It can be seen from this drawing that the coverplate 9 slides on the seal 12 and the coverplate 9 is held by the magnets 13. A narrow slot or gap 26 is formed between the coverplate 9 and the magnets 13 either because a dimension (such as the thickness) of the seal 12 is larger than that of the magnets 13, or because of the relative proximity of the seal 12 and magnets 13 with respect to coverplate 9.

As a result of the mounting of the chamber wall 5 above the holding magnet 19 arranged on the microtome 2, the chamber wall 5 can easily be removed after the object holder 24 has been withdrawn from the chamber 3. That is, the chamber wall 5 is attached to the chamber 3 via the holding magnet 19 and, accordingly, the wall 5 can be easily removed from the body of the chamber 3 thus providing simple access to the microtome 2 for any necessary maintenance work. In addition, the microtome 2 can be released from a holding plate 23 which is attached to the cryostat 25 via connections (not shown) and be demounted completely from the cryostat 25.

After removal of the wall 5, the locating pin 20 which is provided between the chamber wall 5 and the orifice 21 located in the microtome 2, permits the chamber wall 5 to be remounted into its appropriate position.

Figure 3:
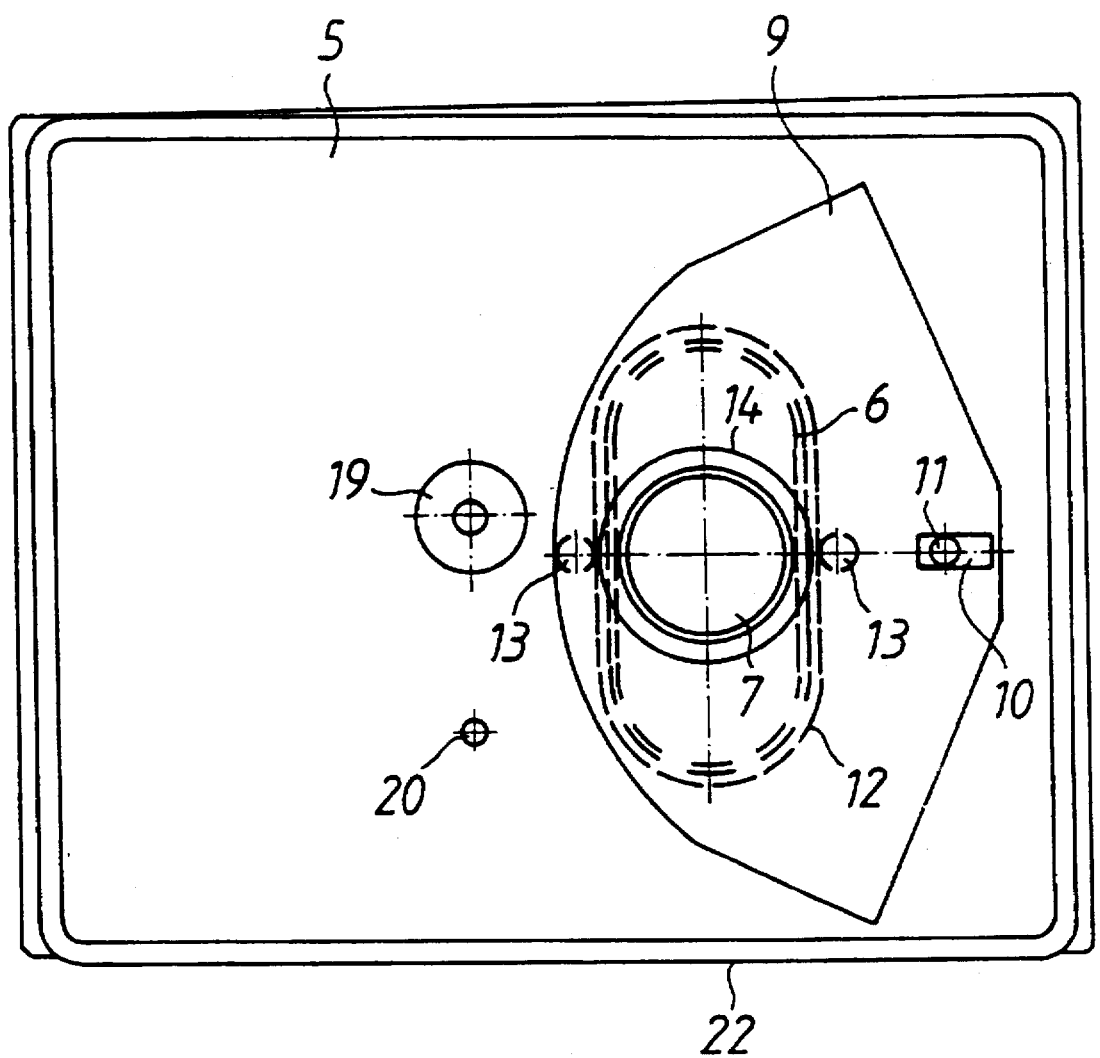
FIG. 3 shows a front view of the chamber wall of the microtome chamber according to the present invention.

FIG. 3 shows a view of the removable chamber wall 5 from the direction of the microtome, with the holding magnet 19, the locating pin 20, the magnets 13 and the peripheral seal 22. The seal 12 is arranged around the periphery of the elongate slot 6 in the chamber wall 5. The coverplate 9 slides on the seal 12 and is equipped with an elongate bearing orifice 10. A pin 11 engages into this bearing orifice 10 and forms the center of rotation for the pivotable coverplate 9. The sleeve 14, through which the object-holding device 7 is inserted, is fastened to the coverplate 9. The linearly oscillating or lateral movement of the object-holding device 7 is transmitted via the sleeve 14 to the coverplate 9 which then moves via the pin 11 on an approximately circular path.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A housing for a microtome which is capable of being employed in a cryostat, said housing comprising:
    an object holding device which is axially movable; and
    a waterproof microtome chamber including a chamber wall, said wall having an elongated slot through which said object holding device extends, said elongated slot having a periphery, and said elongated slot including a seal which is diposed about the periphery of said elongated slot, said slot further being covered by a coverplate which is provided adjacent said seal of said slot,
    said coverplate having an orifice through which a pin having an axis, which is fixedly arranged on the chamber wall, extends such that said coverplate is rotatable about the axis of said pin,
    said chamber further including magnets which are arranged on said wall of said chamber adjacent said elongated slot such that said magnets retain said coverplate over said elongated slot, wherein a sleeve is arranged on the coverplate, and a guide band is arranged between the sleeve and the object holding device, said guide band being capable of transmitting movement of the object holding device to the coverplate.

2. A housing for a microtome as claimed in claim 1, wherein a peripheral seal is arranged between the sleeve and the object holding device.

3. A housing for a microtome as claimed in claim 2, wherein the seal is plastic.

4. A housing for a microtome as claimed in claim 2, wherein the magnets have a thickness which is smaller than the thickness of the seal, so as to form a gap between the magnets and the coverplate.

5. A housing for a microtome as claimed in claim 2, wherein a holding magnet is provided on a microtome which is housed in said housing for releasably fastening the chamber wall to said microtome chamber.

6. A housing for a microtome which is capable of being employed in a cryostat, said housing comprising:
    an object holding device which is axially movable; and
    a waterproof microtome chamber including a chamber wall, said wall having an elongated slot through which said object holding device extends, said elongated slot having a periphery, and said elongated slot including a seal which is disposed about the periphery of said elongated slot, said slot further being covered by a coverplate which is provided adjacent said seal of said slot,
    said coverplate having an orifice the through which a pin having an axis, which is fixedly arranged on the chamber wall, extends such that said coverplate is rotatable about the axis of said pin,
    said chamber further including magnets which are arranged on said wall of said chamber adjacent said elongated slot such that said magnets retain said coverplate over said elongated slot, wherein a holding magnet is provided on a microtome which is housed in said housing for releasably fastening the chamber wall to said microtome chamber, and wherein the chamber wall has a locating pin which is adapted to engage with an orifice provided on the microtome which is located in said housing.

7. A housing for a microtome which is capable of being employed in a cryostat, said housing comprising:
    an object holding device which is axially movable; and
    a waterproof microtome chamber including a chamber wall, said wall having an elongated slot through which said object holding device extends, said elongated slot having a periphery, and said elongated slot including a seal which is disposed about the periphery of said elongated slot, said slot further being covered by a coverplate which is provided adjacent said seal of said slot,
    said coverplate having an orifice through which a pin having an axis, which is fixedly arranged on the chamber wall, extends such that said coverplate is rotatable about the axis of said pin,
    said chamber further including magnets which are arranged on said wall of said chamber adjacent said elongated slot such that said magents retain said coverplate over said elongated slot, wherein said microtome chamber has an outer periphery which is provided with a peripheral seal thereabout.

* * * * *